(12) United States Patent
Helmer

(10) Patent No.: US 11,986,637 B2
(45) Date of Patent: *May 21, 2024

(54) STATE INDICATOR AND DRUG DELIVERY DEVICE WITH A STATE INDICATOR AND A METHOD FOR MANUFACTURING A DRUG DELIVERY DEVICE

(71) Applicant: Sanofi-Aventis Deutschland GMBH, Frankfurt am Main (DE)

(72) Inventor: Michael Helmer, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 125 days.

This patent is subject to a terminal disclaimer.

(21) Appl. No.: 17/552,040

(22) Filed: Dec. 15, 2021

(65) Prior Publication Data

US 2022/0105273 A1  Apr. 7, 2022

Related U.S. Application Data

(63) Continuation of application No. 16/344,558, filed as application No. PCT/EP2017/077167 on Oct. 24, 2017, now Pat. No. 11,207,466.

(30) Foreign Application Priority Data

Oct. 25, 2016 (EP) ..................................... 16195411

(51) Int. Cl.
*A61M 5/28* (2006.01)
*A61M 5/31* (2006.01)
*A61M 5/32* (2006.01)

(52) U.S. Cl.
CPC ........ *A61M 5/28* (2013.01); *A61M 2005/3126* (2013.01); *A61M 5/3243* (2013.01); *A61M 2205/3306* (2013.01); *A61M 2205/50* (2013.01)

(58) Field of Classification Search
CPC .................. A61M 5/28; A61M 5/3243; A61M 2005/3128; A61M 2205/3306; A61M 2205/50
See application file for complete search history.

(56) References Cited

U.S. PATENT DOCUMENTS 5,722,893 A  3/1998  Hill et al.
11,207,466 B2 *  12/2021  Helmer .................. A61M 5/28
(Continued)

FOREIGN PATENT DOCUMENTS

CN  101068586  11/2007
CN  102510762  6/2012
(Continued)

OTHER PUBLICATIONS

International Preliminary Report on Patentability in Application No. PCT/EP2017/077167, dated Apr. 30, 2019, 6 pages.
(Continued)

*Primary Examiner* — Tasnim Mehjabin Ahmed
(74) *Attorney, Agent, or Firm* — Fish & Richardson P.C.

(57) ABSTRACT

The present disclosure relates to a state indicator designed for indicating at least three states (S1 to Sn) of a drug delivery device and formed as a single indicator for indicating a respective state (S1 to Sn) at least before injection, during injection and after injection.

18 Claims, 5 Drawing Sheets

(56) References Cited

U.S. PATENT DOCUMENTS

| | | |
|---|---|---|
| 2012/0041389 A1 | 2/2012 | Giambattista et al. |
| 2013/0079725 A1 | 3/2013 | Shang |
| 2015/0032059 A1 | 1/2015 | Allerdings et al. |
| 2015/0202365 A1 | 7/2015 | Roervig et al. |
| 2015/0258286 A1 | 9/2015 | Mosebach et al. |
| 2016/0001017 A1 | 1/2016 | Ogawa |
| 2016/0213844 A1 | 7/2016 | Benson et al. |
| 2016/0296699 A1 | 10/2016 | Cabiri |
| 2016/0296716 A1 | 10/2016 | Cabiri et al. |
| 2017/0007765 A1 | 1/2017 | Cowe et al. |

FOREIGN PATENT DOCUMENTS

| | | |
|---|---|---|
| CN | 103930141 | 7/2014 |
| CN | 104220116 | 12/2014 |
| CN | 106029134 | 10/2016 |
| EP | 2201971 | 6/2010 |
| GB | 2488579 | 9/2012 |
| JP | 2013-529990 | 7/2013 |
| JP | 2014-526370 | 10/2014 |
| JP | 2015-506770 | 3/2015 |
| WO | WO 2006/058883 | 6/2006 |
| WO | WO 2008/005315 | 1/2008 |
| WO | WO 2008/146021 | 12/2008 |
| WO | WO 2010/100213 | 9/2010 |
| WO | WO 2011/036133 | 3/2011 |
| WO | WO 2012/000838 | 1/2012 |
| WO | WO 2012/164406 | 12/2012 |
| WO | WO 2013/044172 | 3/2013 |
| WO | WO 2013/120777 | 8/2013 |
| WO | WO 2014/122782 | 8/2014 |
| WO | WO 2015/124923 | 8/2015 |
| WO | WO 2016/025316 | 2/2016 |
| WO | WO 2016/050902 | 4/2016 |
| WO | WO 2016/055400 | 4/2016 |
| WO | WO 2016/061220 | 4/2016 |
| WO | WO 2016/083347 | 6/2016 |

OTHER PUBLICATIONS

International Search Report and Written Opinion in Application No. PCT/EP2017/077167, dated Dec. 22, 2017, 8 pages.

* cited by examiner

STATE INDICATOR AND DRUG DELIVERY DEVICE WITH A STATE INDICATOR AND A METHOD FOR MANUFACTURING A DRUG DELIVERY DEVICE

CROSS REFERENCE TO RELATED APPLICATIONS

The present application is a continuation of U.S. application Ser. No. 16/344,558, filed on Apr. 24, 2019, which is the national stage entry of International Patent Application No. PCT/EP2017/077167, filed on Oct. 24, 2017, and claims priority to Application No. EP 16195411.0, filed on Oct. 25, 2016, the disclosures of which are incorporated herein by reference.

TECHNICAL FIELD

The disclosure generally relates to a state indicator for a drug delivery device. The disclosure further relates to a drug delivery device comprising a state indicator and a method for manufacturing a drug delivery device.

BACKGROUND

Administering an injection is a process which presents a number of risks and challenges for users and healthcare professionals, both mental and physical. Such injections can be performed by using injection or drug delivery devices, which are applied either by medical personnel or by patients themselves. Pen type drug delivery devices and autoinjectors have been designed and developed to perform regular injections by persons without formal medical training. This is increasingly common among patients having diabetes where self-treatment enables such patients to conduct effective management of their disease. For example, an insulin dose needed to be injected can be manually selected by turning a dosage knob arranged on a pen device and observing the actual dose from an aperture or dose window of the pen device. The dose is then injected by inserting the needle into a suited skin portion and pressing an injection button of the pen device. To be able to monitor a state of the device, in particular to prevent false handling of the pen device or the autoinjector, it is desirable to provide information related to a condition and/or use of the drug delivery device.

Thus, there remains a need for an improved state indicator for a drug delivery device and an improved drug delivery device with such a state indicator.

SUMMARY

This disclosure relates to an improved state indicator and an improved drug delivery device with such a state indicator and an improved manufacturing method.

Exemplary embodiments are described herein.

The disclosure relates to a state indicator designed for indicating at least three states of a drug delivery device and formed as a single indicator indicating a respective state at least before injection, during injection and after injection. Such a single indicator adapted to indicate at least three states of a drug delivery device allows a simple solution for monitoring different states of the drug delivery device by only one indicator.

In an exemplary embodiment, the state indicator is designed as a removable stand-alone unit. In particular, the state indicator may be configured as an add-on device or stand-alone unit like a clip which can be easily attached to and removed from the drug delivery device. Alternatively the removable stand-alone unit may comprise a force-fit connection element or a form-fit connection element.

In a further exemplary embodiment, the single indicator is formed as a visual indicator. The provided visual indicator allows indicating different states to a user without the requirement of additional components and/or an additional indicator. For instance, the visual indicator may be provided by a transparent window in a housing of the drug delivery device through which at least one mark of the piston rod and/or at least one mark of the needle shroud are visible in different states of the drug delivery device.

Additionally or alternatively, the single indicator is formed as an optical indicator. In particular, the optical indicator may be provided by at least one of an electromagnetic radiation source and optical glasses, e.g. magnifying glass with a zoom function. The optical indicator may comprise at least one electromagnetic radiation source configured to illuminate at least a part of the movable component, at least one optical sensor unit configured to emit infrared radiation and adapted to detect infrared radiation reflected from the movable component and at least one processing unit configured to determine a status data/value as a function of the measured reflected infrared radiation. The optical indicator allows measuring information related to the status, condition and/or use of a drug delivery device, such as an initial state, a delivery state, a final state, an injection state, etc.

In particular, the optical indicator may also be configured as a light emitting diode (LED) emitting infrared radiation, red light, yellow light and/or green light. Infrared radiation emitting diodes are powerful, economical and durable components at least until a wavelength range of 900 nm. Furthermore, emitting infrared radiation allows transmitting through the opaque part of the housing of the drug delivery device and thus reading out status data/value that is covered by the housing and/or by additional layers applied onto the movable component, e.g. a needle shroud, by a movable reading device, e.g. a walk-by reading device. Red/yellow/green light emitting diodes enable indicating the different states of the drug delivery device in an easy way directly by the user and without any additional reading devices.

The provided optical indicator enables indicating the different states of the drug delivery device as well as recording and reading out of the different states. The recording of the different states as well as a resulting state history may be an important factor in monitoring the drug delivery device and the injection sequence/doses or a calculating of future doses.

In a further exemplary embodiment, the single indicator is formed as an electronic indicator. The electronic indicator may be provided by at least one sensor unit configured to determine and detect a movement and/or a position of at least one movable component, e.g. a needle shroud, a piston rod, and at least one processing unit configured to determine a status data/value as a function of the measured movement and/or position of the at least one movable component.

In particular, the sensor unit may be configured to determine a position of the movable component relative to a case of the drug delivery device. The determined relative position of the movable component enables determining a position of a needle shroud, a position of a piston and/or a piston rod, a currently selected dose of medicament contained within the drug delivery device. For indicating the status and/or the value determined by the sensor unit, the electronic indicator further comprises the processing unit in combination with a display unit indicating the status data. The electronic indicator may also comprise a memory unit for storing status data, history data, whereby the status data comprises at least information about pre-injection or initial state, delivery or injection state, final state, used state, dose size, injection time, injection duration and drug type. The electronic indicator allows measuring and indicating information related to the status, condition and/or use of a drug delivery device, such as a pre-injection or initial state, a delivery or injection state, a final or post-injection state, a selected dose, etc, on the display unit.

In an exemplary embodiment, the single indicator is designed for producing at least a pre-injection state before injection, e.g. when the drug delivery device is in a safe state. Additionally, the single indicator is designed for producing an injection state during injection when the injection is provided and a post-injection state when the injection is completed. The disclosure further relates to a drug delivery device adapted to dispense a dose of a medicament, wherein the drug delivery device comprises a state indicator according to the disclosure. The drug delivery device further comprises at least a housing, a container with a needle, a piston rod movable within the container and a needle shroud relatively movable with respect to the housing to cover or uncover the needle.

In particular, the state indicator is associated with the needle shroud to produce at least three state indications depending on different needle shroud positions. For instance, a respective state indication is produced when the needle shroud is in an expanded position before injection, when the needle shroud is unexpanded position during injection or when the needle shroud is an expanded position after injection.

In an exemplary embodiment, the state indicator is designed as a visual indicator. For instance, the visual indicator is formed by a transparent window within the housing through which at least one mark of the piston rod and/or at least one mark of the needle shroud are visible in different states of the drug delivery device. Such a visual indicator allows state indication of the drug delivery device without any additional required parts or components.

In a possible embodiment, the piston rod is marked with a profile e.g. a recess, a hole profile, a color mark and/or a print mark on an outer surface of the piston rod. Additionally or alternatively, the needle shroud is marked with a profile, e.g. a recess, a hole profile, a color mark and/or a print mark on an outer surface of the needle shroud. For instance, an add-on device, in particular a clip-on device, which can be attached onto the drug delivery device, can detect the correct or defined position of the hole or recess or mark, in particular in an inspection area under specified light conditions.

For example, the piston rod and/or the needle shroud may be provided with symbols or a sequence of symbols, e.g. numbers, signs, icons, bars or the like, for visibly indicating a status, a position, e.g. a position of the needle shroud or piston rod with respect to the housing and/or the container, a dose or a selected or remaining dose of medicament. The symbols may be arranged on a part of the movable component that is partly visible through a window, e.g. an aperture or transparent window, arranged within the case such that at least the symbol is visible through the window, which represents the status of the drug delivery device. Due to the visible arrangement of the symbols, a user can be indicated the status of the drug delivery device without any additional parts or components directly on the drug delivery device.

Alternatively, the state indicator may be designed to detect kind of symbols on the piston rod and/or the needle shroud which are invisible for the human eye. In particular, the state indicator may be formed as a camera device, e.g. a CCD camera (CCD=charge coupled device) or infrared camera which may read kind of symbols which are arranged on an invisible component of the drug delivery device. An electronic or optical add-on device, e.g. a clip-on device, could also detect a kind of symbols which is invisible for the human eye but readable for the electronic or optical device. Furthermore, a data matrix or a code can be printed on the glass barrel or container. The data matrix or code may be visible through an inspection window in the housing. This inspection window or area does not confuse the user due to the bad readability of the marking when the black or grey stopper covers the marking background. Additionally, the code or data matrix may be printed with an UV light visible (for the user visible) ink anywhere on the glass barrel or container to prevent product counterfeiting.

In a further exemplary embodiment, the movable piston rod and/or the movable needle shroud may be provided with a metal area printed on the outer surface of at least one of them. In particular, an infrared radiation transmitted through the housing will be reflected when striking the metal area due to suppression of wave propagation beyond the so-called skin depth of metal. That means metal provides high contrast with remaining plastic parts of the drug delivery device when using an infrared light emitting diode as the electromagnetic radiation source. As a result a signal-to-noise ratio may be substantially high. Here, a stand-alone or add-on unit with an optical or electronic indicator or a walk-by reading device allows indication of the status of the drug delivery device.

The drug delivery device may be configured such that visible light is allowed to transmit through the window in order to visibly indicate the status of the drug delivery device represented by the symbols or marks on the at least one movable component and/or such that infrared radiation is allowed to be transmitted through the opaque part of the case in order to illuminate at least the movable component comprising the status data. This configuration enables the common window for the user adapted to visibly indicate the different state of the drug delivery device at the same position without requiring an additional window or aperture.

In an exemplary embodiment, the state indicator is formed as a stand-alone unit which is removably mountable to the housing. In particular, the stand-alone unit comprises an optical or electronic indicator. For example, the optical indicator is a light source e.g. is a light emitting diode with an integrated position or distance sensor determining the position and/or distance, movement of at least one of the movable component, e.g. of the needle shroud and/or the piston and/or the piston rod. In another exemplary embodiment, the stand-alone unit comprises an electronic indicator with an integrated position or distance sensor with an outer display unit.

A drug delivery device in combination with the status indicator may comprise a housing and at least one movable component received within the housing, whereby both are components of the drug delivery device. The at least one movable component is movable with respect to the housing and is provided with different marks assigned to a different states each representing a status of the drug delivery device. The marks are arranged on a part of the movable component.

In particular, the needle shroud and the plunger rod are coaxially arranged to each other and axially moveable relative to each other and relative to the housing. The needle shroud is arranged between the plunger rod and the housing. The plunger rod is axially moveable relative to the housing as well as to the container and to the needle shroud when the needle shroud is in a retracted position in which the needle extends out of the needle shroud. The needle shroud is relatively movable with respect to the housing as well as to the container between an extended position in which the needle is covered by the needle shroud and the retracted position in which the needle is covered.

According to a further embodiment the state indicator comprises a window, aperture or recess arranged proximally to the container within the housing. For example, the recess is arranged in the housing wall in a position or level near a stopper or proximal end of the container. In different states of the drug delivery device, different components, e.g. the stopper, the piston rod and/or the needle shroud are positioned in this area. For example in the pre-injection position, the stopper is visible in this area. During injection, the piston rod is visible and after injection the needle shroud is visible in this area and thus, through the respective transparent window or recess within the housing.

Furthermore, at least one of the profile and marks on the piston rod and the needle shroud is relatively positioned with respect to the window. For instance, during injection, a symbol, mark printed on the needle shroud is visible through the window in the housing. Further marks, symbols provided on other components, e.g. on a stopper or the container, may be used. In a pre-filled stopper position, e.g. a data matrix or another code printed on the container is visible through the container and the window in the housing. In case that the code or data matrix is not visible through the container, the state indicator may be designed as a respective sensor which reads the data through the housing, e.g. by an infrared camera or other suitable sensor.

The needle shroud and the plunger rod are relatively assembled to each other in an assembled state of the drug delivery device in such a manner that the profile and marks on the piston rod and the needle shroud are relatively aligned to each other. Therefore, in different states of the drug delivery device, at least one of the different marks or symbols printed on the different components, e.g. on the piston rod, the stopper, the container and/or the needle shroud, is visible through the same window within the housing of the drug delivery device. This allows that the user needs only to look at the one window in the housing of the drug delivery device. The window is integrated at such a position of the drug delivery device that is visible in all respective states of the drug delivery device.

The drug delivery device is for example designed as an auto-injector device. The drug delivery device is supplied as a self-contained device. Such device has a pre-filled cartridge or container, e.g. a pre-filled syringe with a pre-selected dose. The drug delivery device may be a disposable device, e.g. a device which does not provide for an exchange of an empty container.

According to another aspect of the invention, a method for manufacturing a drug delivery device is provided wherein a state indicator is provided and arranged relatively within or onto the drug delivery device. The state indicator may be a stand-alone unit which may be removably attached to the outer housing of the drug delivery device. Alternative the state indicator may be provided as an integrated part of the drug delivery device, e.g. as an aperture or recess in the housing. The components are such assembled and relatively moveable with respect to each other and aligned to each other that through the aperture or recess different components, e.g. the stopper, the piston rod and/or the needle shroud, are visible at different states of the drug delivery.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 5 ml).

In combination with a specific medicament, the presently described devices may also be customized in order to operate within required specifications. For example, the device may be customized to inject a medicament within a certain time period (e.g. about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle sleeve, or other activation component. Activation may be a one-step or multi-step process. That is, a user may need to activate one or more activation mechanism in order to cause the automated function. For example, a user may depress a needle sleeve against their body in order to cause injection of a medicament. In other devices, a user may be required to depress a button and retract a needle shield in order to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1A:
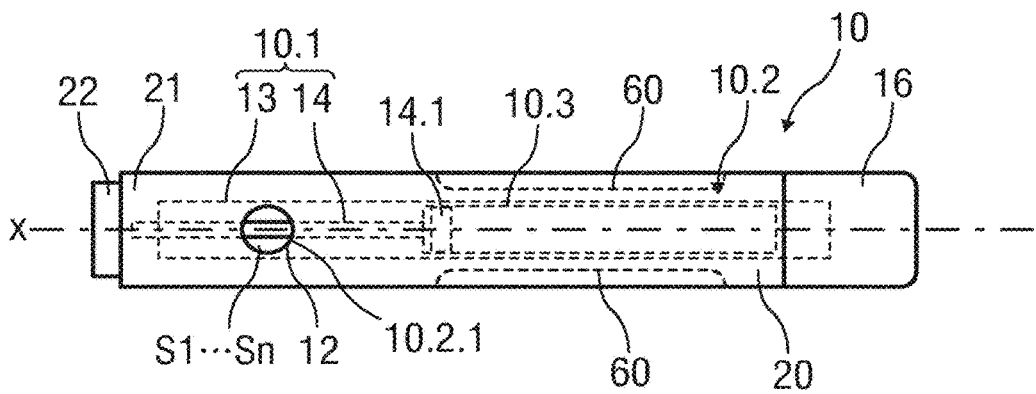
FIG. 1A to 1B is a schematic perspective view of an exemplary embodiment of a drug delivery device comprising a housing and a cap assembly.
Figure 1B:
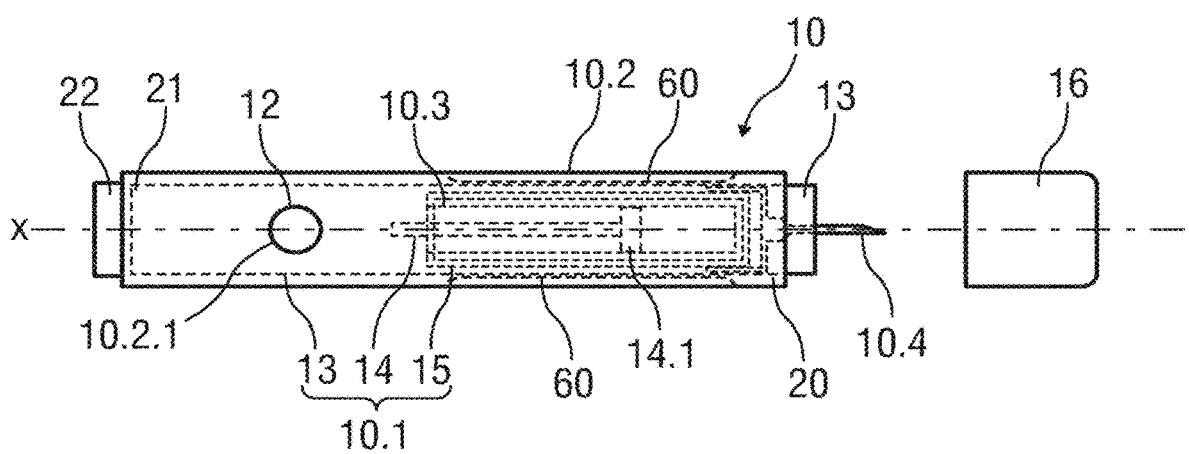

According to some embodiments of the present disclosure, an exemplary drug delivery device 10 is shown in FIGS. 1A & 1B. Device 10, as described above, is configured to inject a medicament into a patient's body. Device 10 includes a housing 10.2 which typically contains a container 10.3 or a reservoir containing the medicament to be injected (e.g., a syringe) and the components required to facilitate one or more steps of the delivery process. Device 10 can also include a cap assembly 16 that can be detachably mounted to the housing 10.2. Typically a user must remove cap assembly 16 from housing 10.2 before device 10 can be operated.

As shown, housing 10.2 is substantially cylindrical and has a substantially constant diameter along the longitudinal axis X. The housing 10.2 has a distal region 20 and a proximal region 21. The term "distal" refers to a location that is relatively closer to a site of injection, and the term "proximal" refers to a location that is relatively further away from the injection site.

Device 10 can also include as a moveable component 10.1 at least one of a needle sleeve or shroud 13 and a piston rod 14 and a syringe carrier 15. The sleeve 13 is coupled to housing 10.2 to permit movement of sleeve 13 relative to housing 10.2. For example, sleeve 13 can move in a longitudinal direction parallel to longitudinal axis X. Specifically, movement of sleeve 13 in a proximal direction can permit a needle 10.4 to extend from distal region 20 of housing 10.2. The piston rod 14 comprises a piston 14.1 which is axially displaceable in the container 10.3.

Insertion of needle 10.4 can occur via several mechanisms. For example, needle 10.4 may be fixedly located relative to housing 10.2 and initially be located within an extended needle sleeve 13. Proximal movement of sleeve 13 by placing a distal end of sleeve 13 against a patient's body and moving housing 10.2 in a distal direction will uncover the distal end of needle 10.4. Such relative movement allows the distal end of needle 10.4 to extend into the patient's body. Such insertion is termed "manual" insertion as needle 10.4 is manually inserted via the patient's manual movement of housing 10.2 relative to sleeve 13.

Another form of insertion is "automated," whereby needle 10.4 moves relative to housing 10.2. Such insertion can be triggered by movement of sleeve 13 or by another form of activation, such as, for example, a button 22. As shown in FIGS. 1A & 1B, button 22 is located at a proximal end of housing 10.2. However, in other embodiments, button 22 could be located on a side of housing 10.2.

Other manual or automated features can include drug injection or needle retraction, or both. Injection is the process by which a bung or piston 14.1 is moved from a proximal location within a container 10.3 to a more distal location within the container 10.3 in order to force a medicament from the container 10.3 through needle 10.4. The needle 10.4 is configured as a needle assembly with a needle 10.4 comprising a needle hub which is attachable to the container 10.3.

In other embodiments, the device 10 may comprise a drug window 60 in the housing 10.2. The drug window 60 allows a view on the container 10.3. The drug window 60 extends in the longitudinal direction and may have a length similar to the length of the container 10.3. In some embodiments, the device 10 may comprise two opposing drug windows 60 in the housing 10.2. The drug windows 60 may be configured as a recess or aperture in the housing 10.2. Alternatively, the drug window 60 may be configured as a transparent area in the housing 10.2.

In another form, the container 10.3 may be configured as a prefilled syringe with a needle attached to it. The container 10.3 may be arranged within the syringe carrier 15.

In some embodiments, a drive spring (not shown) is under compression before device 10 is activated. A proximal end of the drive spring can be fixed within proximal region 21 of housing 10.2, and a distal end of the drive spring can be configured to apply a compressive force to a proximal surface of piston 14.1.

Following activation, at least part of the energy stored in the drive spring can be applied to the proximal surface of piston 14.1. This compressive force can act on piston 14.1 to move it in a distal direction. Such distal movement acts to compress the liquid medicament within the container 10.3, forcing it out of needle 10.4.

Following injection, needle 10.4 can be retracted within sleeve 13 or housing 10.2. Retraction can occur when sleeve 13 moves distally as a user removes device 10 from a patient's body. This can occur as needle 10.4 remains fixedly located relative to housing 10.2. Once a distal end of sleeve 13 has moved past a distal end of needle 10.4, and needle 10.4 is covered, sleeve 13 can be locked. Such locking can include locking any proximal movement of sleeve 13 relative to housing 10.2.

Another form of needle retraction can occur if needle 10.4 is moved relative to housing 10.2.

Such movement can occur if the syringe within housing 10.2 is moved in a proximal direction relative to housing 10.2. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 10.4 and housing 10.2 can be locked with a locking mechanism. In addition, button 22 or other components of device 10 can be locked as required.

The drug delivery device 10 can comprise a state indicator 12 for indicating at least three states S1 to Sn of the drug delivery device 10. The state indicator 12 is formed as a single indicator for indicating a respective state S1 to Sn of the drug delivery device 10 at least before injection, during injection and after injection. In an exemplary embodiment, the state indicator 12 is formed as a window in the housing 10.2 through which different movable components 10.1 or part of these components 10.1, e.g. at least one of the needle sleeve 13 and piston rod 14, are visible at the various states S1 to Sn.

Figure 1C:
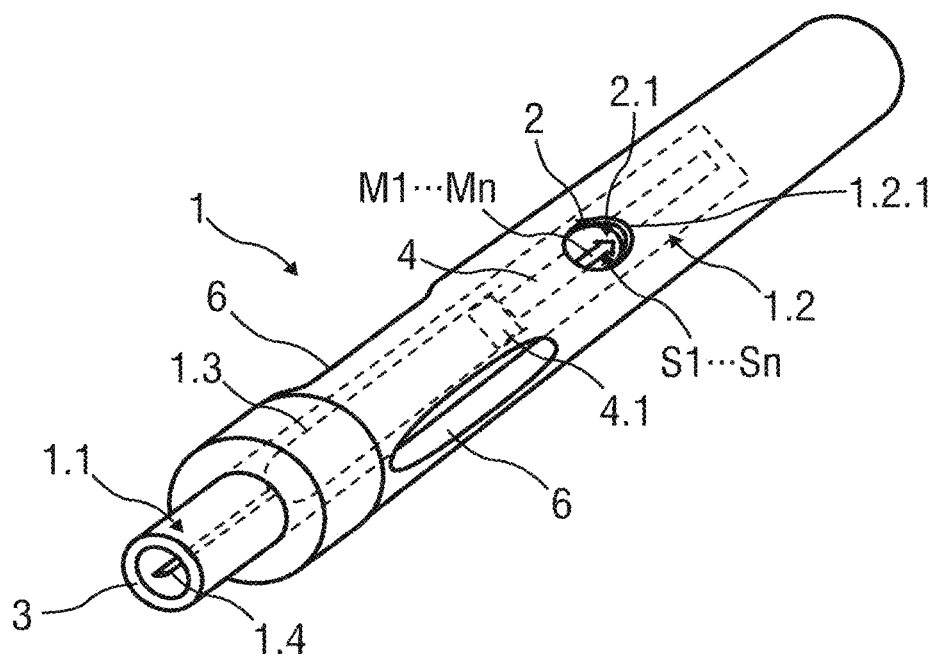
FIG. 1C is a schematic perspective view of an exemplary embodiment of a drug delivery device comprising a movable component.

FIG. 1C shows a schematic perspective view of an exemplary embodiment of a drug delivery device 1. The drug delivery device 1 comprises at least one movable component 1.1. The component 1.1 is relatively movable with respect to a housing 1.2 of the drug delivery device 1.

The drug delivery device 1 may be configured as a pre-filled, disposable injection pen or as an autoinjector comprising the housing 1.2 receiving the movable component 1.1 and at least a container 1.3 to which a needle 1.4 may be fixed. The needle 1.4 may be protected by an inner needle cap and an outer needle cap, e.g. a so called needle shield (not illustrated).

The drug delivery device 1 comprises a state indicator 2 for indicating at least three states S1 to Sn of the drug delivery device 1. The state indicator 2 is formed as a single indicator for indicating a respective state S1 to Sn of the drug delivery device 1 at least before injection, during injection and after injection.

The state indicator 2 is designed as a single indicator. The single indicator is designed in an exemplary embodiment as a visual indicator 2.1. The visual indicator 2.1 comprises at least a window 1.2.1 in the housing 1.2. The window 1.2.1 may be configured as a transparent area or as an aperture in the housing 1.2. In an exemplary embodiment, the drug delivery device 1 may comprise two opposing windows 1.2.1 in the housing 1.2.

The drug delivery device 1 comprises further a drug window 6. The drug window 6 is formed for example as a longitudinal recess, an aperture or a transparent area in the housing 1.2. In an exemplary embodiment, the drug delivery device 1 comprises two opposing drug windows 6 in the housing 1.2. The drug window/s 6 allow/s a view on the container 1.3, in particular on the drug in the container 1.3.

In an exemplary embodiment, the drug window 6 has larger dimensions than the window 1.2.1. For example, the drug window 6 extends in a longitudinal direction and its length is larger than its width.

The drug window 6 or each of the drug windows 6 is/are spaced apart to the state indicator 2. In particular, the drug window 6 is spaced apart to the window 1.2.1 in the housing 1.2. In more detail, the drug window 6 or each of the drug windows 6 is/are spaced apart to the state indicator 2, in particular to the window 1.2.1 in longitudinal direction as well as angularly. The window 1.2.1 has for example a round shape.

The movable component 1.1 may be designed as a needle shroud 3 which is movably received within the housing 1.2 and with respect to the housing 1.2.

The state indicator 2, in particular the visual indicator 2.1, is associated with the needle shroud 3 to produce the at least three state indications depending on different needle shroud positions.

Figure 5:
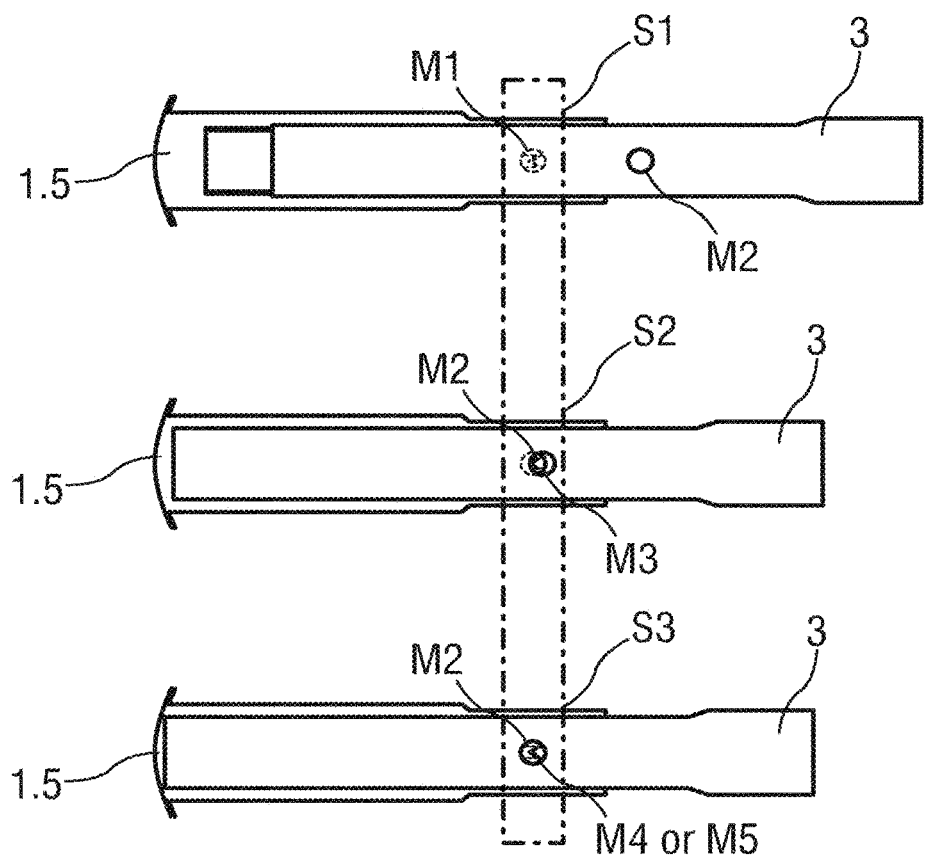
FIG. 5 is a schematic side view of a cut-out of an exemplary embodiment of the drug delivery device in different states.

In particular, the visual indicator 2.1 indicates a first status S1 when the needle shroud 3 is in an expanded position before injection (shown in FIGS. 1 and 5), a second status S2 when the needle shroud 3 is in an unexpanded position during injection (shown in FIG. 5) and a third status S3 when the needle shroud 3 is an expanded position after injection (shown in FIG. 5).

The respective state S1 to Sn is displayed through the window 1.2.1 arranged within the housing 1.2. The respective state S1 to Sn may be represented by mark M1 to Mn printed or laser marked spirally around an outer circumference of the movable component 1.1. The mark M1 to Mn may be printed as numbers, icons, bars, holes, colored symbols or the like.

Additionally or alternatively, the movable component 1.1 may be designed as a piston rod 4 and/or a piston 4.1 which are movably received within the container 1.3 and with respect to the container 1.3.

In a further exemplary embodiment, hence, the state indicator 2, in particular the visual indicator 2.1, is associated with the needle shroud 3 and/or the piston rod 4 and/or the piston 4 to produce the at least three state indications depending on different needle shroud/piston/piston rod positions.

Figure 2:
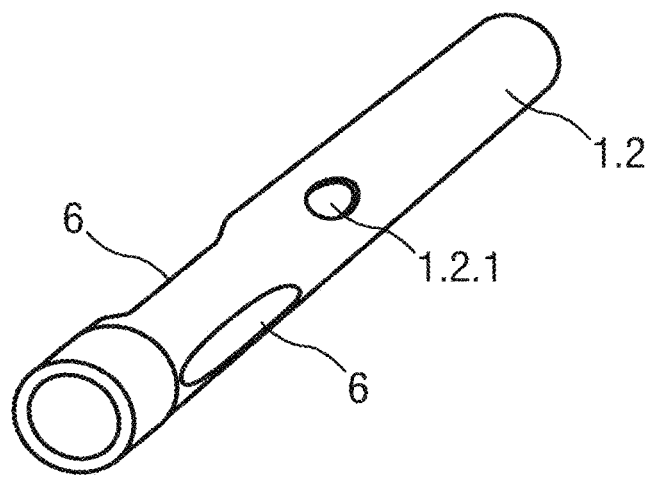
FIG. 2 is a schematic perspective view of an exemplary embodiment of a housing of the drug delivery device.

FIG. 2 shows a schematic perspective view of an exemplary embodiment of a housing 1.2 of the drug delivery device 1. The window 1.2.1 is a transparent part of the housing 1.2 permeable for visible light and may have dimensions enabling displaying exactly one mark M1 to Mn provided by the needle shroud 3, the piston 4.1 and/or the piston rod 4. For example, the window 1.2.1 is configured as an aperture.

Figure 3:
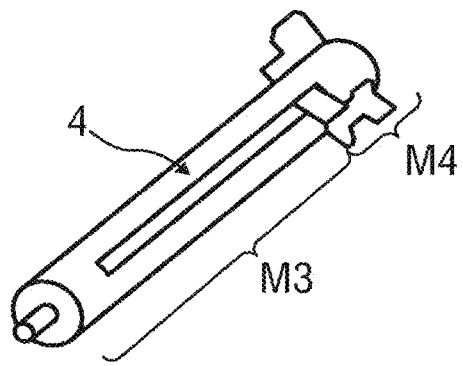
FIG. 3 is a schematic perspective view of an exemplary embodiment of a piston rod of the drug delivery device.

FIG. 3 shows a schematic perspective view of an exemplary embodiment of a piston rod 4 of the drug delivery device 1. The piston rod 4 comprises different mark M3, M4 which are associated with at least two states S3 to S4.

In particular, mark M3 is associated with the state S3 which represent that the drug delivery device 1 is in an injection state. For example a colored outer surface of the piston rod 4 is visible through the window 1.2.1 of housing 1.2 during injection.

The mark M4 is associated with the state S4 which represent that the injection of the drug delivery device 1 is completed. For example another colored outer surface of the piston rod 4 or a symbol or a print on the piston rod 4 is visible through the window 1.2.1 of housing 1.2 at the end of injection.

Figure 4:
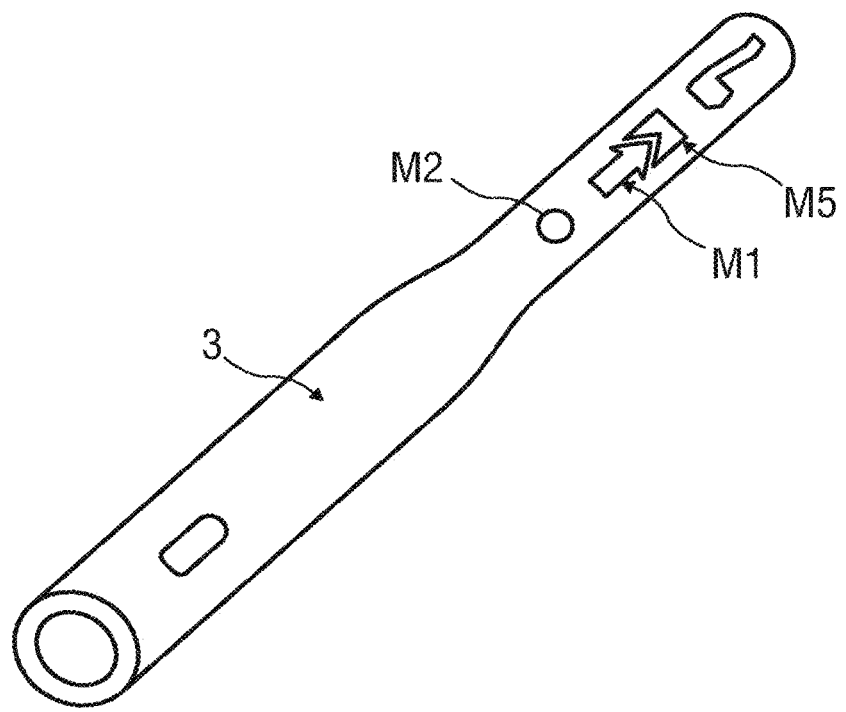
FIG. 4 is a schematic perspective view of an exemplary embodiment of a needle shroud of the drug delivery device.

FIG. 4 shows a schematic perspective view of an exemplary embodiment of a needle shroud 3 of the drug delivery device 1. The needle shroud 3 comprises different marks M1, M2 and M5 which are associated with at least two states S1, S2, S5.

In particular, mark M1 is associated with the state S1 which represent that the drug delivery device 1 is in a pre-injection or initial state. For example a colored outer surface of the needle shroud 3 or a symbol or a print on the needle shroud 3 is visible through the window 1.2.1 of housing 1.2 before injection.

The mark M2 is associated with the state S2 which represents that the drug delivery device 1 is in an injection state or in a final state. For example, another colored outer surface of the needle shroud 3 or a hole within the needle shroud 3 or a symbol or a print on the needle shroud 3 is visible through the window 1.2.1 of the housing 1.2 during or after injection. In particular, through the hole within the needle shroud 3 one of the marks M3, M4 of the piston rod 4 is visible.

The mark M5 is associated with the state S5 which represents that the drug delivery device 1 is in a post-injection or final state. For example another colored outer surface of the needle shroud 3 or a hole within the needle shroud 3 or a symbol or a print on the needle shroud 3 is visible through the window 1.2.1 of the housing 1.2 in the post-injection state, in particular when the needle shroud 3 is finally locked to prevent a re-using.

FIG. 5 shows a schematic side view of a cut-out of an exemplary embodiment of the drug delivery device 1 in different states S1 to S3, in particular in status S1 before injection, in status S2 during injection and in status S3 when the injection is completed. The drug delivery device 1 comprises a rear housing part 1.5. The needle shroud 3 is movably received within the housing part 1.5 as best seen from the sequence of views.

In status S1, the mark M1 of the needle shroud 3 is visible through the window 1.2.1 of the housing 1.2 before injection.

In status S2, the mark M2 of the needle shroud 3 is designed as an aperture within the needle shroud 3 so that the mark M3 of the piston rod 4 is visible through the window 1.2.1 of the housing 1.2 during injection.

In status S3, the mark M2 of the needle shroud 3 is designed as an aperture within the needle shroud 3 so that the mark M4 of the piston rod 4 or the mark M5 of the needle shroud 3 is visible through the window 1.2.1 of the housing 1.2 at the end of injection before the needle shroud 3 is locked or after injection (post-injection) when the needle shroud 3 is locked against re-using of the drug delivery device 1.

Figure 6:
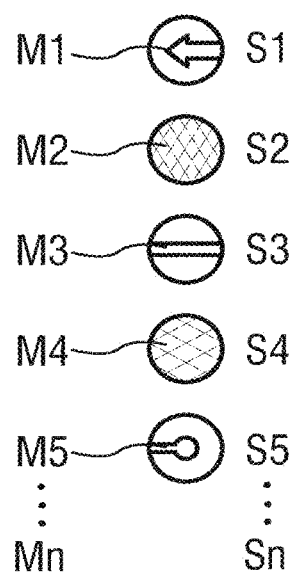
FIG. 6 is a schematic view of different marks assigned to the different states of the drug delivery device.

FIG. 6 shows a schematic view of different marks M1 to Mn assigned to the different states S1 to Sn of the drug delivery device 1.

The mark M1 is for example a print on an outer surface of the needle shroud 3 representing that the drug delivery device 1 is a pre-injection status S1.

The marks M2 and M3 are examples for a coloured movable component 1.1, e.g. for a partially coloured needle shroud 3 or a partially coloured piston rod 4 representing that the drug delivery device 1 is in a start status S2 before injection or in an injection status S3 during injection.

The mark M4 is an example for a coloured movable component 1.1, e.g. for a partially coloured needle shroud 3 or a partially coloured piston rod 4 representing that the injection of the drug delivery device 1 is completed. For example, once the piston 4.1 has reached a distal end of the container 1.3, it is ensured by the mark M4 that indication to the user that injection of the product is completed is given only once the product is substantially expelled from the container 1.3.

The mark M5 is for example a print on an outer surface of the needle shroud 3 representing that the drug delivery device 1 is in a post-injection status S5 in which the needle shroud 3 is for example locked.

Figure 7:
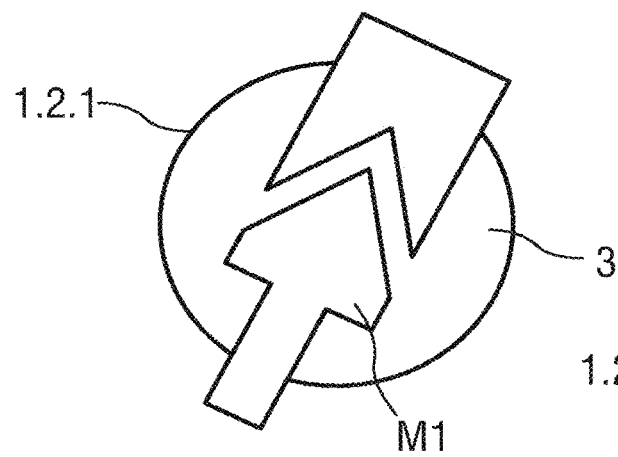
FIG. 7 is a schematic view of a mark represented by a print onto a needle shroud and assigned to pre-injection state of the drug delivery device.
Figure 8:
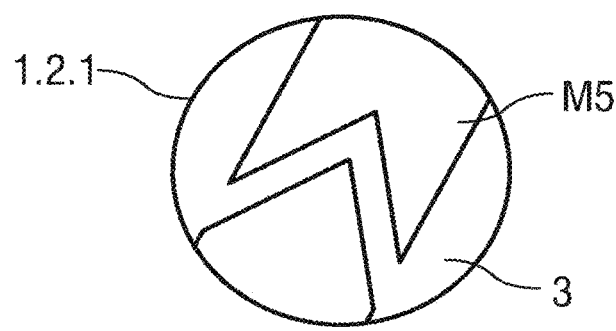
FIG. 8 is a schematic view of a mark represented by a print onto a needle shroud and assigned to post-injection state of the drug delivery device.

FIGS. 7 and 8 show further schematic views of other possible marks M1, M5 represented by a print onto the needle shroud 3 and assigned to pre-injection state S1 or post-injection state S5 of the drug delivery device 1. The marks M1, M5 are visible through the window 1.2.1 of the housing 1.2.

Figure 9:
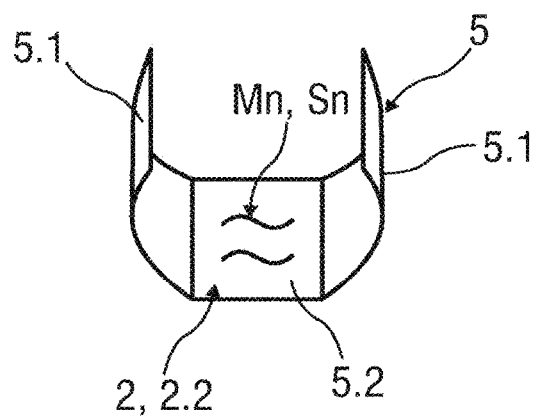
FIGS. 9, 10 are schematic perspective views of an exemplary embodiment of a stand-alone unit which may be removably attached to the drug delivery device.

FIG. 9 shows a schematic perspective view of an embodiment of a stand-alone unit 5 as an example for an electronic indicator 2.2 which may be removably attached to the drug delivery device 1. According to this embodiment an additional part is necessary. The stand-alone unit 5 may be designed as a clip which may be removably attached to the housing 1.2 of the drug delivery device 1. Alternatively, the stand-alone unit 5 may comprise force-fit or form-fit connecting elements 5.1 to removably attach the unit 5 onto the housing 1.2 or another holder to hold the device 5 onto the housing 1.2.

In particular, the connecting elements 5.1 are formed as arms extending form the electronic indicator 2.2. The arms are flexible and form clamping arms which engage and clamp the stand-alone unit 5 to the drug delivery device 1. The clamp arms are lengthened and biased radially to retain the stand-alone unit 5

The stand-alone unit 5 may comprise a display unit 5.2 for indicating different states Sn of the drug delivery device 1.

Alternatively the stand-alone unit 5 may be structured as an optical unit, e.g. as an optical glass, for example as a magnifying glass with zoom function to enlarge marks, symbols or profiles provided on the drug delivery device 1.

Figure 10:
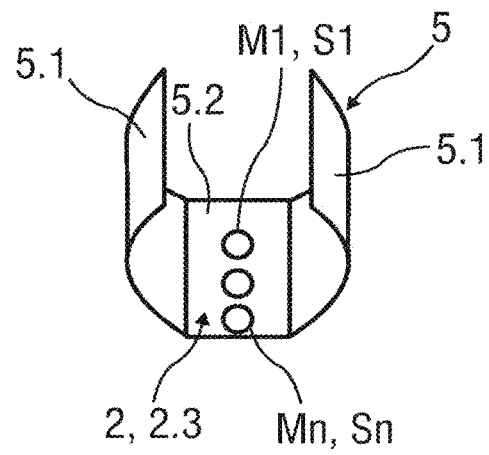

FIG. 10 shows another exemplary embodiment for a stand-alone unit 5 which may be designed as an optical indicator 2.3. The optical indicator 2.3 comprises at least one light source as a mark M1 to Mn. For example the light source is a light emitting diode wherein only one light emitting diode may be represented different states S1 to Sn of the drug delivery device 1. Alternatively, the optical indicator 2.3 comprises a number of light sources wherein each of them is associated with one of the different states S1 to Sn.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 amino acid peptide which is produced by the salivary glands of the Gila monster), Liraglutide/ Victoza, Semaglutide, Taspoglutide, Syncria/Albiglutide, Dulaglutide, rExendin-4, CJC-10.234-PC, PB-1023, TTP-054, Langlenatide/HM-10.2260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1, 10 drug delivery device
1.1, 10.1 movable component
1.2, 10.2 housing
1.2.1, 10.2.1 window
1.3, 10.3 container
1.4, 10.4 needle
1.5 housing part
2, 12 state indicator
2.1 visual indicator
2.2 electronic indicator
2.3 optical indicator
3, 13 needle shroud
4, 14 piston rod
4.1, 14.1 piston
5.1 connecting element
5.2 display unit
5 display unit
6, 60 drug window
15 syringe carrier
16 cap assembly
20 distal region
21 proximal region
22 button
M1 to Mn mark
S1 to Sn status
X longitudinal axis

The invention claimed is:

1. A state indicator comprising:
an outer housing structure which is designed for indicating a number of states of a drug delivery device,
wherein the state indicator is configured to indicate a current state of the drug delivery device selected from at least three states based on respective marks located on a movable component of the drug delivery device, the at least three states comprising:
a pre-injection state before injection,
an injection state during the injection when the injection is being performed, and
a post-injection state when the injection is completed,
wherein the state indicator is formed as an electronic indicator, and
wherein the state indicator is designed as an add-on device which can be attached to and removed from the drug delivery device.

2. The state indicator according to claim 1, wherein the add-on device comprises the electronic indicator and connecting elements extending from the electronic indicator and forming clamping arms.

3. The state indicator according to claim 1, wherein the state indicator is configured to be associated with a needle shroud of the drug delivery device to indicate the at least three states depending on at least one of different needle shroud positions or piston rod positions.

4. The state indicator according to claim 1, wherein the state indicator is configured to detect at least one of a mark of a piston rod of the drug delivery device or a mark of a needle shroud of the drug delivery device that is visible in different states of the drug delivery device through a window in a housing of the drug delivery device.

5. The state indicator according to claim 4, wherein the window is configured to be arranged proximally to a container within the housing of the drug delivery device.

6. The state indicator according to claim 5, wherein:
the window is positionable relative to at least one of a profile, a color mark, or a print mark on at least one of the piston rod or the needle shroud of the drug delivery device.

7. A drug delivery device comprising:
a housing;
a container with a needle;
a piston rod movable with respect to the container;
a needle shroud relatively movable with respect to the housing; and a state indicator comprising:
an outer housing structure which is designed for indicating a number of states of the drug delivery device,
wherein the state indicator is configured to indicate a current state of the drug delivery device selected from at least three states based on respective marks located on a movable component of the drug delivery device, the at least three states comprising:
a pre-injection state before injection,
an injection state during the injection when the injection is being performed, and
a post-injection state when the injection is completed,
wherein the state indicator is formed as an electronic indicator.

8. The drug delivery device according to claim 7, wherein the housing of the drug delivery device comprises a drug window.

9. The drug delivery device according to claim 7, wherein the state indicator is associated with the needle shroud to indicate the at least three states depending on at least one of different needle shroud positions or piston rod positions.

10. The drug delivery device according to claim 7, wherein the drug delivery device comprises a window in the housing of the drug delivery device through which at least one mark of the piston rod or the needle shroud is visible in different states of the drug delivery device.

11. The drug delivery device according to claim 7, wherein at least one of the piston rod or the needle shroud is marked with at least one of a profile, a color mark, or a print mark.

12. The drug delivery device according to claim 11, wherein at least one of the profile, the color mark, or the print mark is arranged on an outer surface of at least one of the piston rod and the needle shroud directed towards the housing of the drug delivery device.

13. The drug delivery device according to claim 7, wherein the state indicator is designed as an add-on device which is removably mountable to the housing of the drug delivery device.

14. The drug delivery device according to claim 7, wherein the needle shroud and the piston rod are coaxially arranged to each other and axially moveable relative to each other and relative to the housing of the drug delivery device.

15. The drug delivery device according to claim 7, wherein the drug delivery device comprises a window arranged proximally to the container within the housing of the drug delivery device.

16. The drug delivery device according to claim 15, wherein:
at least one of the piston rod or the needle shroud is marked with at least one of a profile, a color mark, or a print mark, and
at least one of the profile, the color mark, or the print mark on at least one of the piston rod or the needle shroud is relatively positioned with respect to the window.

17. The drug delivery device according to claim 7, wherein both the piston rod and the needle shroud are marked with at least one of a profile or a mark, and wherein the needle shroud and the piston rod are relatively aligned to each other in such a manner that the at least one of the profile or the mark on the piston rod and the at least one of the profile and the mark on the needle shroud are relatively aligned to each other.

18. The drug delivery device according to claim 7, wherein the container is prefilled with a drug.

* * * * *